United States Patent [19]
Brucker et al.

[11] Patent Number: 5,279,563
[45] Date of Patent: Jan. 18, 1994

[54] DIGITAL DISPLAY FOR AN INFLATION SYSTEM FOR A BALLOON CATHETER

[75] Inventors: Gregory G. Brucker, Minneapolis; Duane Zytkoviez, Onamia; Thomas J. McEvoy, Minnetonka, all of Minn.

[73] Assignee: B. Braun Medical, Inc., Plymouth, Minn.

[21] Appl. No.: 887,763

[22] Filed: May 22, 1992

Related U.S. Application Data

[63] Continuation-in-part of Ser. No. 604,650, Oct. 29, 1990, abandoned.

[51] Int. Cl.$^5$ .......................................... A61M 29/00
[52] U.S. Cl. ..................................... 604/98; 604/219
[58] Field of Search ................. 604/181, 218, 96–100; 114, 118, 119, 187, 21 B, 207, 208, 209, 210, 211, 219, 220, 222, 224, 228

[56] References Cited

U.S. PATENT DOCUMENTS

| | | | |
|---|---|---|---|
| 938,544 | 11/1909 | Ball | 604/224 |
| 4,500,310 | 2/1985 | Christinger | 604/228 |
| 4,723,938 | 2/1988 | Goodin et al. | 604/97 |
| 4,743,230 | 5/1988 | Nordquist | 604/224 |
| 4,872,483 | 10/1989 | Shah | 604/100 |
| 5,019,041 | 5/1991 | Robinson et al. | 604/97 |
| 5,021,046 | 6/1991 | Wallau | 604/97 |
| 5,047,015 | 9/1991 | Foote et al. | 604/99 |

*Primary Examiner*—C. Fred Rosenbaum
*Assistant Examiner*—Manuel Mendez
*Attorney, Agent, or Firm*—Hugh D. Jaeger

[57] ABSTRACT

An inflation system for pressurization and depressurization of a balloon catheter. The inflation system includes a syringe, including a syringe barrel, a plunger with expandable thread, a handle with cam, a syringe end cap, and a digital pressure gauge. The syringe is structured such that part of the syringe barrel has an internal thread which engages the expandable threads of the plunger. In the disengaged mode, the plunger slides freely within the syringe barrel allowing for rapid motion to purge, pressurize, or depressurize the inflation system. Once pressure reaches a predetermined level in the system, the cam on the handle causes the threads to automatically lock against the syringe barrel, and continued pressurization or depressurization is accomplished by the rotation of the plunger handle with respect to the syringe barrel. One advantage of the inflation system is that only one step is necessary for locking the syringe for controlled pressurization and depressurization. A digital display engages to a pressure port to indicate the pressure and displays absolute pressure and elapsed time at absolute pressure. In addition, the digital display provides for a communication interface to a data acquisition system such as a personal computer to record date, time and pressure over finite term periods.

1 Claim, 16 Drawing Sheets

DIGITAL DISPLAY FOR AN INFLATION SYSTEM FOR A BALLOON CATHETER

CROSS REFERENCE TO CO-PENDING APPLICATIONS

This patent application is a continuation of U.S. Ser. No. 07/604,650, filed Oct. 29, 1990, now abandoned, entitled "Hemostasis Value Introducer" to the same assignee, which relates to U.S. Ser. No. 07/601,431 filed Oct. 23, 1990, now abandoned, entitled "Inflation System for a Balloon Catheter" to the same assignee as the present patent application.

BACKGROUND OF THE INVENTION

1. Field of the Invention

This patent application pertains to a medical device and more specifically, pertains to a digital display for an inflation system for a balloon catheter.

2. Description of the Prior Art

Inflation devices are currently used in several vascular procedures, the most of which is balloon angioplasty. During this procedure, a balloon catheter is inserted into peripheral artery and is moved through the vasculature to the coronary arteries, where it is positioned the lesion to be dilated. The inflation device is then attached to the proximal end of the balloon catheter, and mechanical force is applied to the fluid in the balloon via the inflation device. The appropriate pressure is maintained on the balloon until reshaping of the atherosclerotic lesion is complete. A vacuum is then created by the inflation device to facilitate removal of the balloon from the vasculature.

Prior art pressure displays are analog meters operating on the deflection of a mechanical entity with application of pressure. Specifically, a bourden tube gauge with a C-shaped planar form and a rectangular cross section expands when pressurized. The C-portion is connected to a linkage which turns the needle for indicating pressure. The disadvantages of this technology are difficulty in providing medically clean passages in the gauge, lack of readability of gauge under low level lighting, need for another instrument to measure time, and inability to automatically and permanently record history of the inflation.

The present invention overcomes the disadvantages of the prior art by providing a digital display for an inflation system for a balloon catheter. The digital display digitizes the pressure and presents the pressure information and elapsed time on a digital display, and also provides for storage of such information on a data acquisition system, such as a personal computer. In addition, most sensors are sealed, providing for convenient mounting to the device with minimal and easily cleaned passageways.

SUMMARY OF THE INVENTION

The general purpose of the present invention is a digital display for display of pressure and elapsed time for an inflation system for a balloon catheter, including a digital communications interface to a data acquisition system, such as a personal computer.

An inflation syringe for use with the present invention is a 20 cc disposable inflation device with an integral digital pressure gauge, a two-part plunger assembly with an automatic lock/release mechanism, a flexible high pressure extension tube, and a three-way stopcock. The device may be operated in any one of four modes.

In the first mode, the inflation syringe can function as a normal syringe. This occurs when the system is at a low pressure, such as when the unit is being primed. During priming the handle/plunger assembly is free to move within the syringe barrel body so that contrast media can be drawn into the syringe by withdrawing the plunger assembly, and then air is purged from the inflation syringe barrel by pointing it upward and slowly advancing the plunger to expel air from the syringe barrel and extension tube.

In the second mode, the inflation syringe can function as a means to pressurize a distensible or compliment medical device such as a balloon catheter.

This is accomplished by moving the plunger handle inwardly. Initially, the handle/plunger assembly is free to move within the syringe barrel similar to that of the primary mode. Once significant resistance to axial movement is encountered, i.e., system compliance has been eliminated, the plunger will automatically lock in position. System pressure can then be increased by clockwise rotation of the plunger handle. This rotation will advance the plunger to increase the system pressure to the desired level. The integral analog pressure gauge will indicate system pressure.

In the third mode, balloon depressurization and balloon deflation can be accomplished slowly or rapidly. Slow balloon depressurization and deflation is accomplished by counterclockwise rotation of the plunger handle. This rotation will allow direct control of the system pressure decay down to approximately 2 ATM.

Rapid balloon deflation can be accomplished by pulling back on the plunger handle to unlock the plunger. This motion will unlock the plunger so that the plunger is free to be retracted.

In the fourth mode, a suction vacuum is maintained by the syringe. This is accomplished by pulling on the handle until the plunger locks against the syringe barrel. This vacuum can be released by moving the handle forward.

The automatic locking of the inflation syringe plunger is accomplished through the design of the plunger/handle assembly. The handle assembly is a separate piece from the plunger assembly and is free to move axially, relative to the plunger. The handle has a cam-shaped profile that bears against an inner ridge on the locking expander portion of the plunger. The locking expander is essentially four leaf springs with molded threads in the center of each section. The rear inner portion of the syringe barrel has matching threads so that when the threads on the locking expanders are expanded, the plunger is locked into position relative to the syringe barrel.

The locking threads engage both in the pressure and vacuum mode. In the pressure mode, as the handle is pushed forward, the plunger also is pushed forward raising the pressure in the system. The system pressure acts on the face of the plunger and resists its forward movement. This force causes the cam on the handle to expand the locking expander until the locking threads engage the syringe barrel, and the plunger is locked into position.

Pushing the handle further locks the handle into a stable position so that it no longer needs to be held to maintain system pressure. This locking action occurs at approximately 2 ATM system pressure.

A similar action occurs at negative pressure when the handle is pulled back, except the locking action occurs at about ½ ATM.

The inflation syringe, operated as described above, has the capability to easily inflate balloons to 20 ATM.

A significant aspect and feature of the present invention is an integrally attached digital display which can be used with an inflation system for a balloon catheter to display pressure for an elapsed time interval, and can be connected to a personal computer through the communications port. The computer, preferably a personal computer, is programmed with the appropriate software to record the date, time and pressure over time periods in which the inflation device has been pressurized.

One significant aspect and feature of the inflation system is the ease of use. The user of the device is not required to perform separate motions or operations to change the device from the priming mode (free plunger travel either direction) to the pressurization/depressurization mode (plunger locked, rotate to advance). The autolocking feature of the device works in conjunction with the system pressure and the user's natural movement, i.e. pushing the plunger of a syringe increases pressure, while pulling on the plunger decreases pressure. Some competing designs require the user to move a release lever to allow free movement of the plunger. Often this lever movement is backward to the natural movement, i.e. the lever must be pulled while the plunger is being pushed.

Another significant aspect and feature of the inflation system is its quiet operation. The only noise heard as the autolock system engages is a slight click which gives the user some audible feedback that locking has occurred. Several of the competing design devices which have a normally engaged plunger locking mechanism make a loud grating noise if the plunger is advanced without holding the release mechanism. This noise can be very disconcerting to the patient and distracting to the attending staff.

A further significant aspect and feature of the inflation system is the small number of parts for the system. This lesser amount leads to a very cost effective device which is inherently more reliable.

Having thus described the preferred embodiments of the present invention, it is a principal object hereof to provide a digital display for an inflation system for a balloon catheter.

One object of the present invention is a digital display for an inflation system for a balloon catheter which is integrally attached to any inflation device.

Another object of the present invention is a digital display which has a communications port which is an integral part of the digital display device.

A further object of the present invention is a digital device which can operate in conjunction with software which is compatible with a personal computer, such as an IBM compatible computer.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
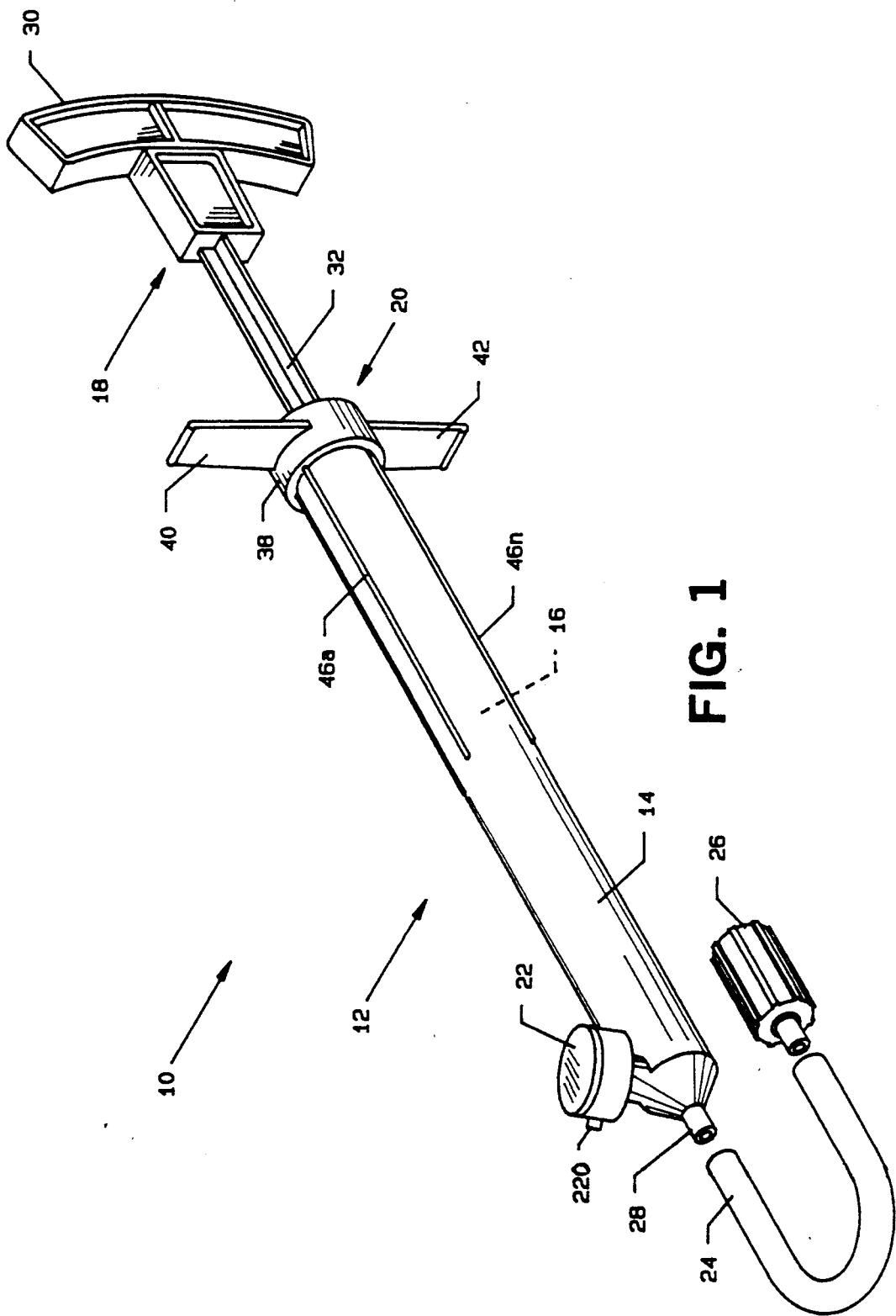
FIG. 1 illustrates an inflation system with a digital display for a balloon catheter, the present invention.

FIG. 1 illustrates an inflation system 10 for a balloon catheter. The inflation system 10 includes a syringe 12 which includes a syringe barrel 14, a plunger 16 illustrated in FIG. 2, a handle 18 in sliding engagement with the plunger 16, a syringe end cap 20 engaged over and about one end of the syringe barrel 14, and an integral analog pressure gauge 22 engaging one end of the syringe barrel 14. A flexible tube 24 connects to the cylindrical outlet 28 of the syringe barrel 14 and a high pressure rotating connector 26 connects to one end of the flexible tube 24.

Figure 2:
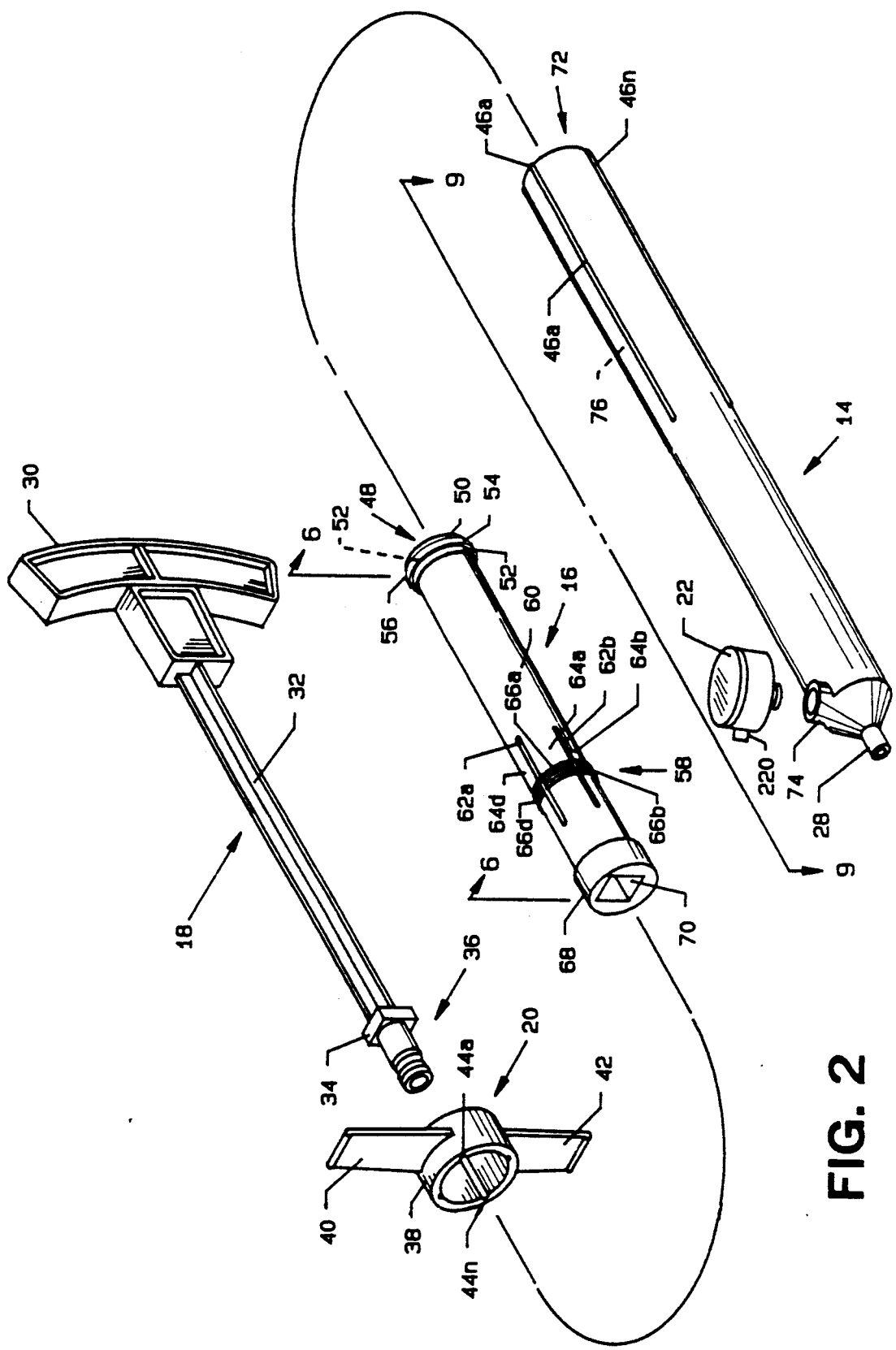
FIG. 2 illustrates an exploded view of the plunger of the inflation system for a balloon catheter.

FIG. 2 illustrates an exploded view of the plunger 12 where all numerals correspond to those elements previously described. The handle 18 includes a t-handle 30, a cruciform shaft 32 extending from the t-handle 30, a square cam 34 opposing the t-handle 30 on the cruciform shaft 32 and a multi-mode cam 36 adjacent to and aligned with the square cam 34. The syringe end cap 20 includes a central cylindrically shaped member 38, and opposing t-handles 40 and 42 extending perpendicularly from the outer circumference of the cylindrically shaped member 38. A plurality of grooves 44a–44n align horizontally and longitudinally along and about the inner circumference of the cylindrically shaped member 38. Grooves 44a–44n of the syringe end cap align over and about ribs 46a–46n on the syringe barrel 14.

The plunger 16 is cylindrically shaped having a closed end 48 adjacent to an annular ring 50 about the plunger 16. Another annular ring 52 aligns about the plunger 16 and is spaced a short distance from the annular ring 50 to form an annular groove 54 about the plunger 16. A round wiper seal ring 56 aligns between the annular rings 50 and 52 in the annular groove 54. A locking expander 58 aligns along the cylindrical body 60. A plurality of elongated holes including elongated holes 62a, 62b, 62c and 62d are spaced about the circumference of the cylindrical body 60 and align horizontally along the cylindrical body 60. The material between adjacent elongated holes 62a-62d form a plurality of leaf springs including leaf springs 64a, 64b, 64c and 64d which are flexed outwardly by the multi-mode cam 36 on the handle 18. A plurality of threaded surfaces including threaded surfaces 66a, 66b, 66c and 66d are located on the outer surface of the leaf springs 64a-64n, respectively. A wide annular ring 68 corresponding to a like radius of annular rings 50 and 52 aligns at one end of the plunger 16 and includes a centrally aligned square hole 70 of a dimension just slightly larger than that of the square cam 34 on the handle 18. The square hole 70 slidingly accommodates the square cam 34 of the handle 18. This arrangement couples the handle 18 to the plunger 16 so that rotational movement of the handle 18 drives the plunger 16 in a corresponding rotational movement.

Figure 9:
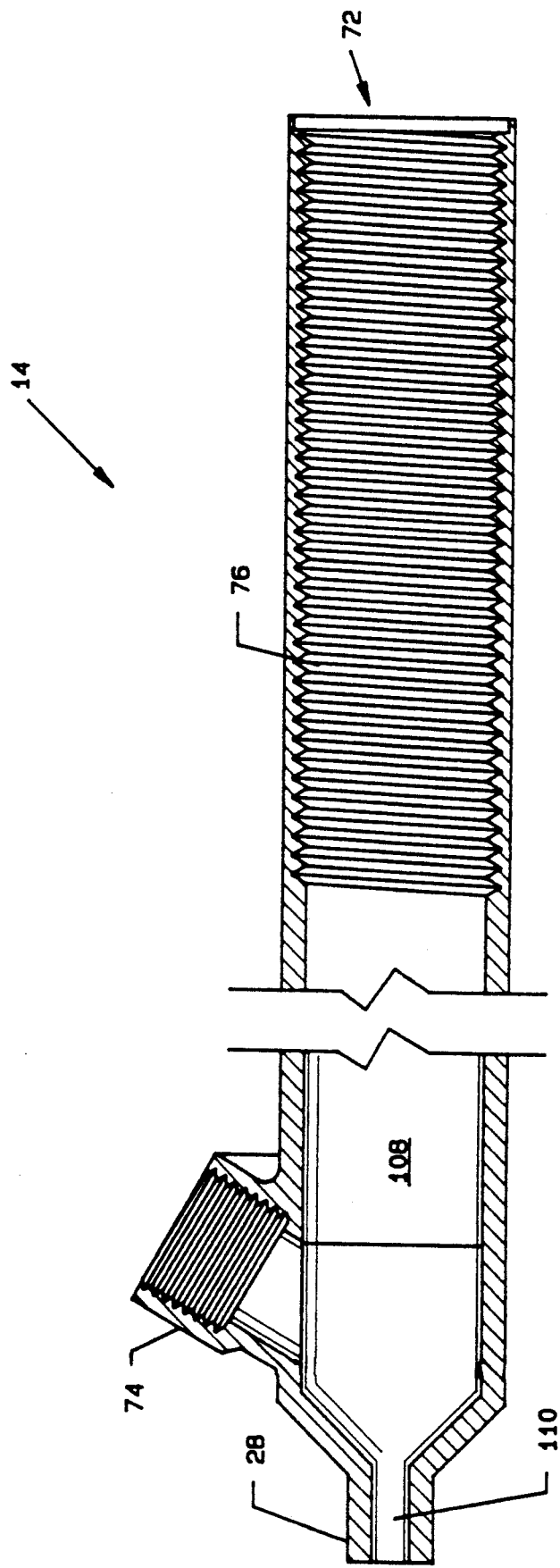
FIG. 9 illustrates a cross section of the syringe barrel along line 9—9 of FIG. 2.

The syringe barrel 14 is cylindrically shaped including an open end 72 for accommodation of the plunger 16 and an opposing end which includes a cylindrically shaped outlet 28. Ribs 46a-46n extend above the cylindrical surface of the syringe barrel to accommodate the grooves 44a-44n of the syringe end cap 20. A threaded ramped member 74 extends from one end of the syringe barrel 14 nearest the cylindrical outlet 28 and is plumbed to the interior of the syringe barrel 14. The pressure gauge 22 is accommodated by the threaded ramped member 74. The interior of the syringe barrel 14 is threaded generally beneath the area of the ribs 46a-46n for engagement with the threaded portions 66a-66d of the leaf springs 64a-64d. These interior threads 76 are illustrated in FIG. 9.

Figure 3:
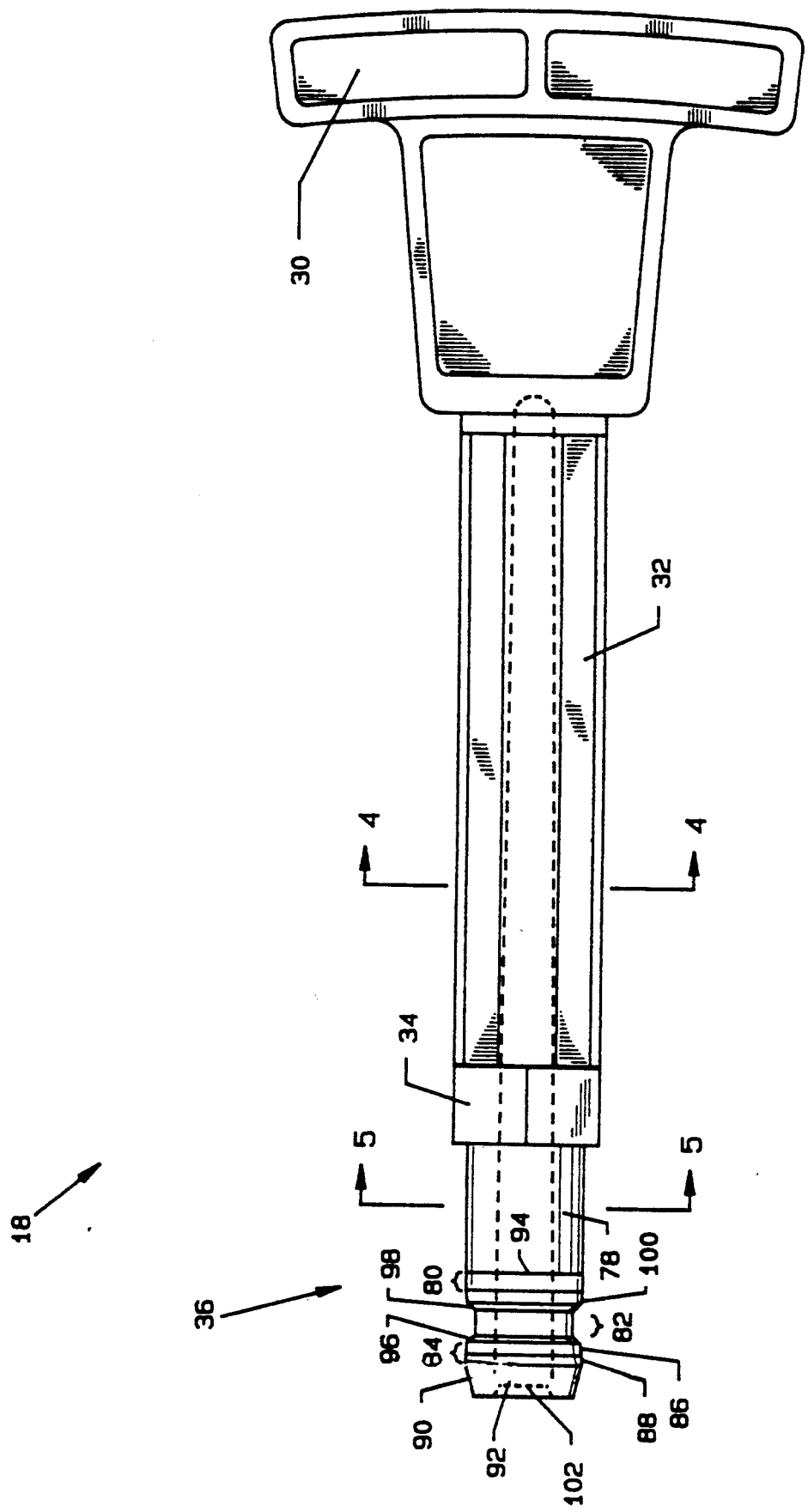
FIG. 3 illustrates a side view of the handle of the inflation system for a balloon catheter.

FIG. 3 illustrates a side view of the handle 18 where all numerals correspond to those elements previously described. The multi-mode cam 36 includes a plurality of cams each having a small ramped portion therebetween. An untapered cylindrical member 78 extends along the center line of the handle 18 followed by cams 80, 82 and 84 in succession. Cam 84 is made up of a ramp 86 and an untapered portion 88. A tapered tip 90 aligns adjacent to the cam 84 to facilitate initial loading of the handle 18 into the plunger 16. The radius of the cylindrical member 78 and the largest radius of the tapered tip 90 are equal to each other. The largest radius of the cam 84 and the radius of the cam 80 are equal but slightly less than that of the mentioned radii of the tapered tip 90 and the cylindrical member 78. The differences in the aforementioned radii form annular stop surfaces 92 and 94 as illustrated. A ramp 96 is located between cams 84 and 82 and ramps 98 and 100 align between ramps 82 and 80 as illustrated. These cams and ramps interact with cams on the underside of the leaf springs 64a-64d as later described in detail. A hole 102 aligns centrally through the cruciform shaft 32, the square cam 34 and the multi-mode cam 36.

Figure 4:
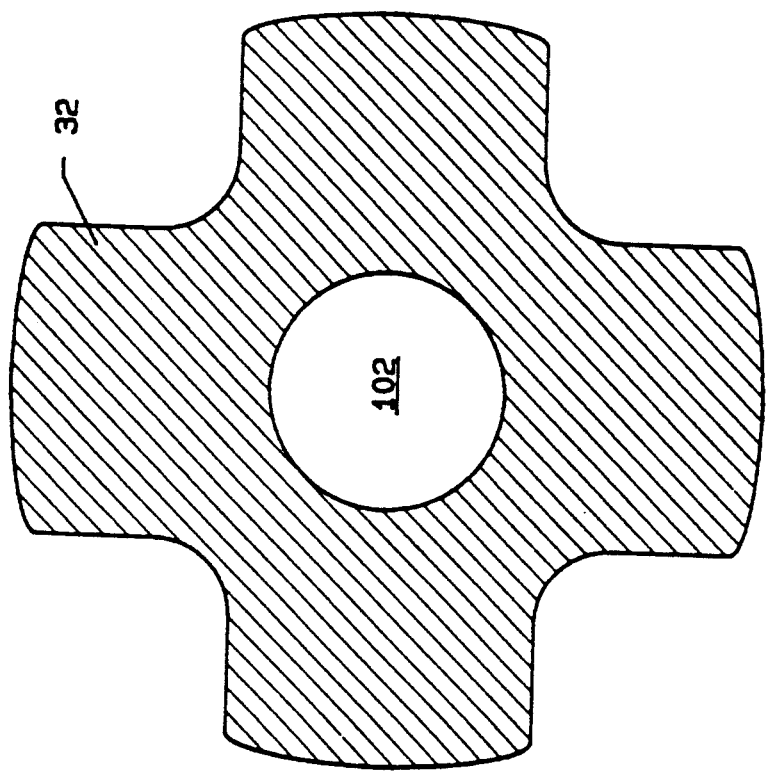
FIG. 4 illustrates a cross section of the cruciform shaft along line 4—4 of FIG. 3.

FIG. 4 illustrates a cross section of the cruciform shaft 32 along line 4—4 of FIG. 3 where all numerals correspond to those elements previously described.

Figure 5:
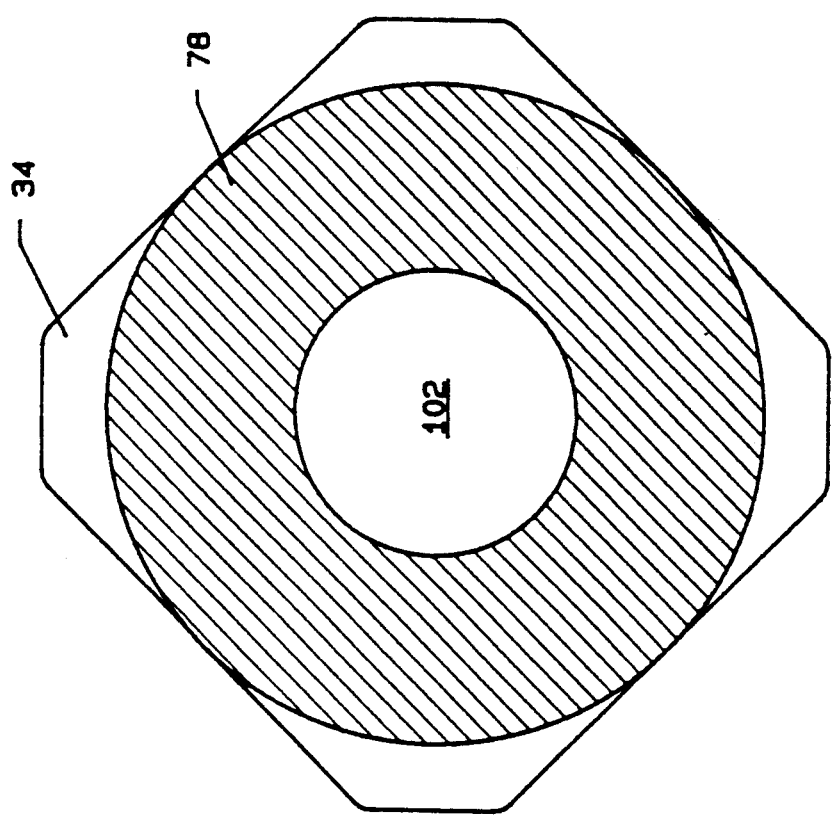
FIG. 5 illustrates a cross section of the multi-mode cam including the square cam along line 5—5 of FIG. 3.

FIG. 5 illustrates a cross section of the multi-mode cam 36 including the square cam 34 along line 5—5 of FIG. 3.

Figure 6:
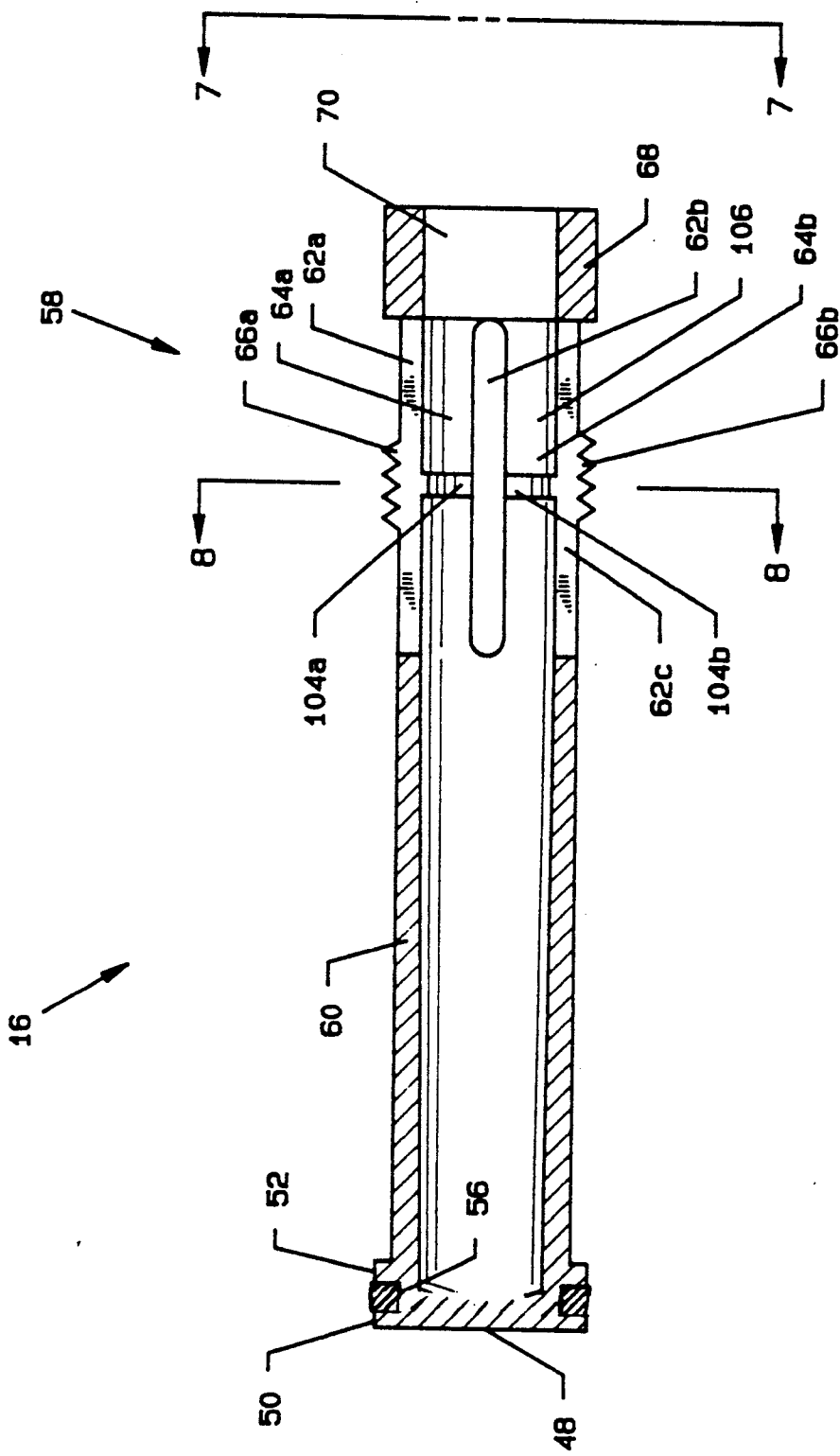
FIG. 6 illustrates a cross section of the plunger along line 6—6 of FIG. 2.

FIG. 6 illustrates a cross section of the plunger 16 along line 6—6 of FIG. 2 where all numerals correspond to those elements previously described. Illustrated in particular are the plurality of cams including cams 104a, 104b, 104c and 104d, also illustrated in FIG. 8, located on the underside of the leaf springs 64a-64d. The interior of the plunger 16 is also round and includes a hole 106 into which the multi-mode cam 36 of the handle 18 is inserted.

Figure 7:
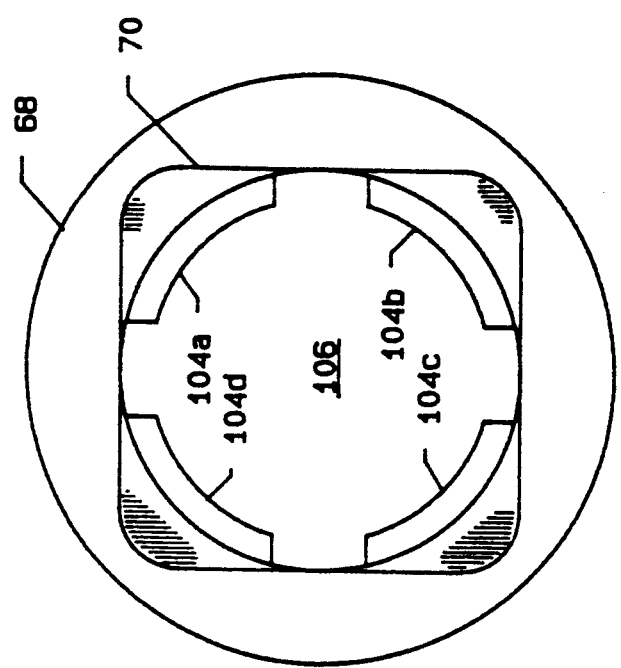
FIG. 7 illustrates a view of the plunger along line 7—7 of FIG. 6.
Figure 11:
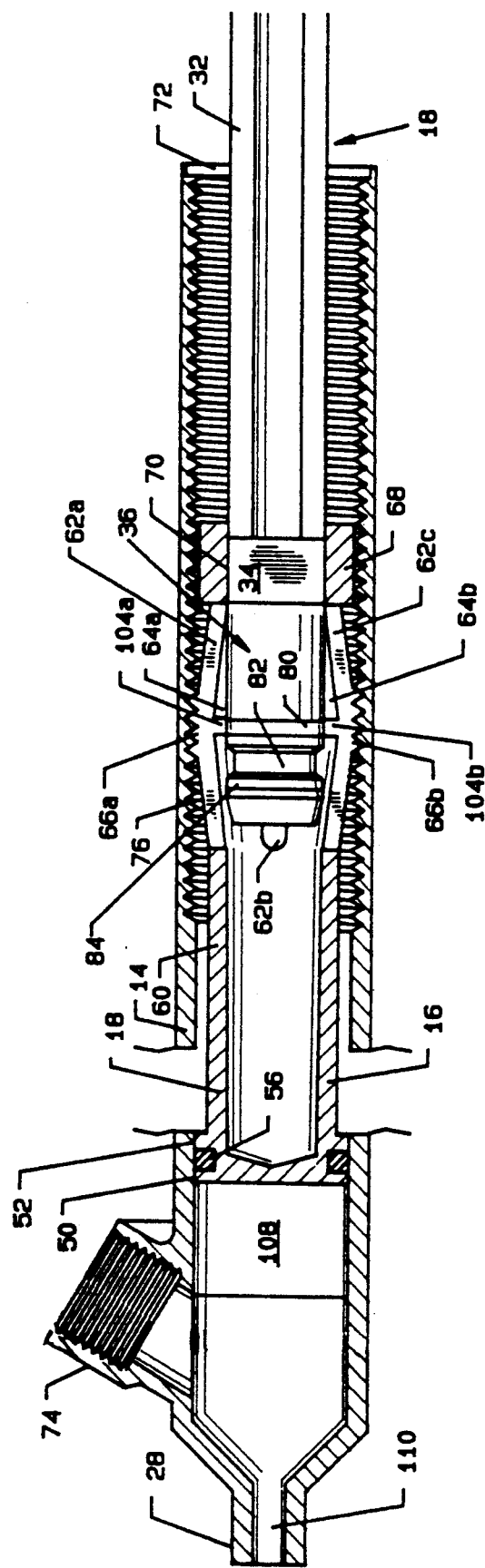
FIG. 11 illustrates the second and third mode of operation of the inflation system for a balloon catheter.
Figure 12:
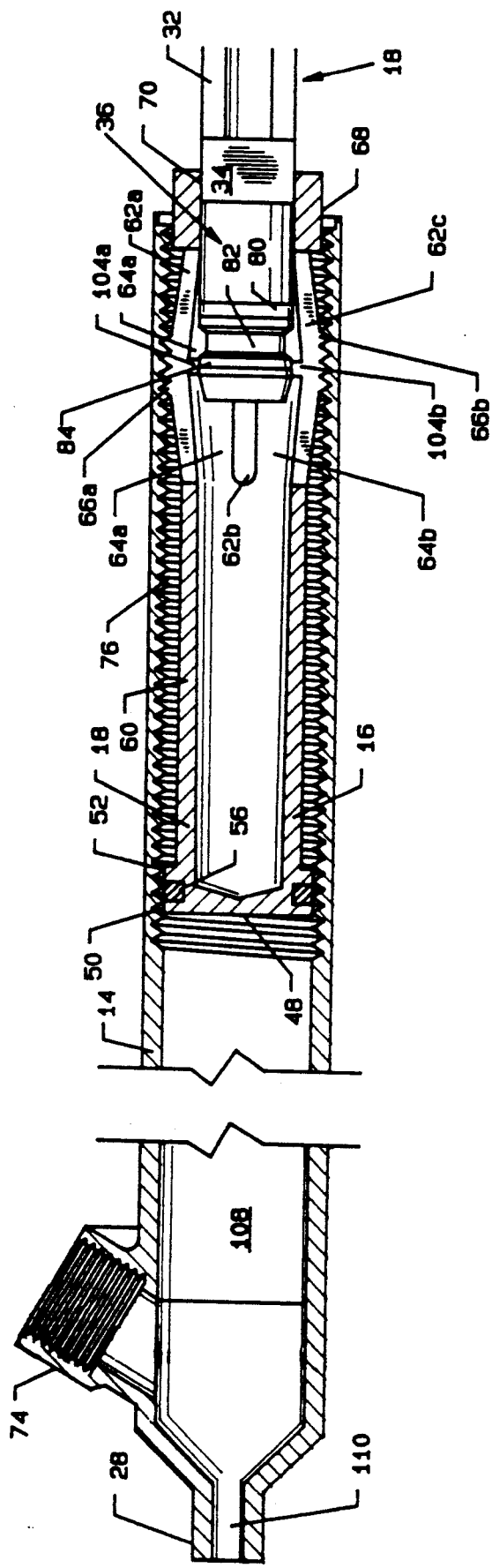
FIG. 12 illustrates the fourth mode of operation of the inflation system for a balloon catheter.

FIG. 7 illustrates a view of the plunger 16 along line 7—7 of FIG. 6 where all numerals correspond to those elements previously described. Illustrated in particular is the shape of the cams 104a-104d which are located on the underside of the leaf springs 64a-64d. The cams 104a-104d are portions of annular rings each of which in unison contact either cam 80, 82 or 84 as illustrated in FIGS. 10, 11 and 12 to position the leaf springs and toothed portions as illustrated.

Figure 8:
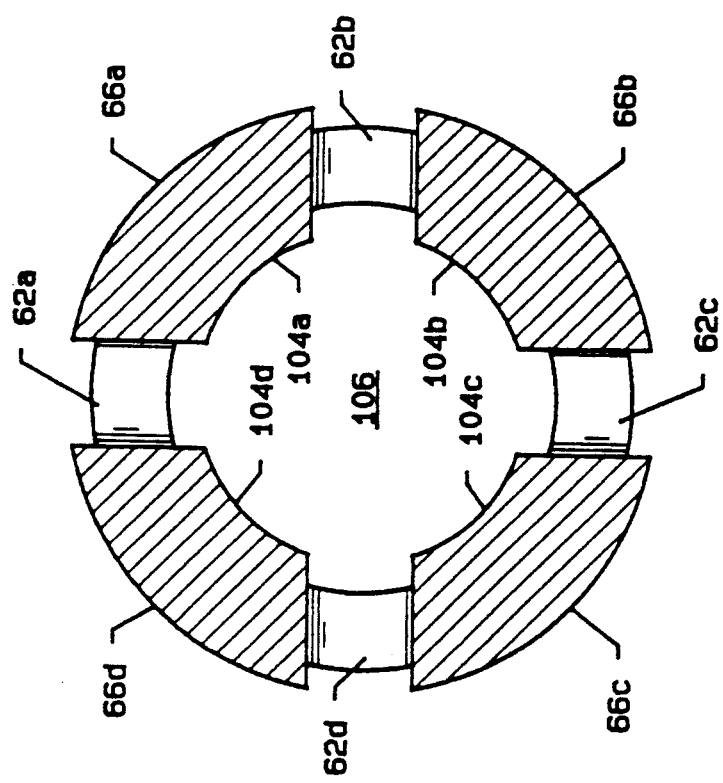
FIG. 8 illustrates cross section view of the threaded surfaces and the cams of the locking expander along line 8—8 of FIG. 6.

FIG. 8 illustrates a cross section view of the threaded surfaces 66a-66d and the cams 104a-104d of the locking expander 58 along line 8—8 of FIG. 6 where all numerals correspond to those elements previously described.

FIG. 9 illustrates a cross section of the syringe barrel 14 along line 9—9 of FIG. 2 where all numerals correspond to those elements previously described. The interior 108 of the syringe barrel 14 is cylindrical in shape and tapers down to a small orifice 110 in the outlet 28.

Figure 10:
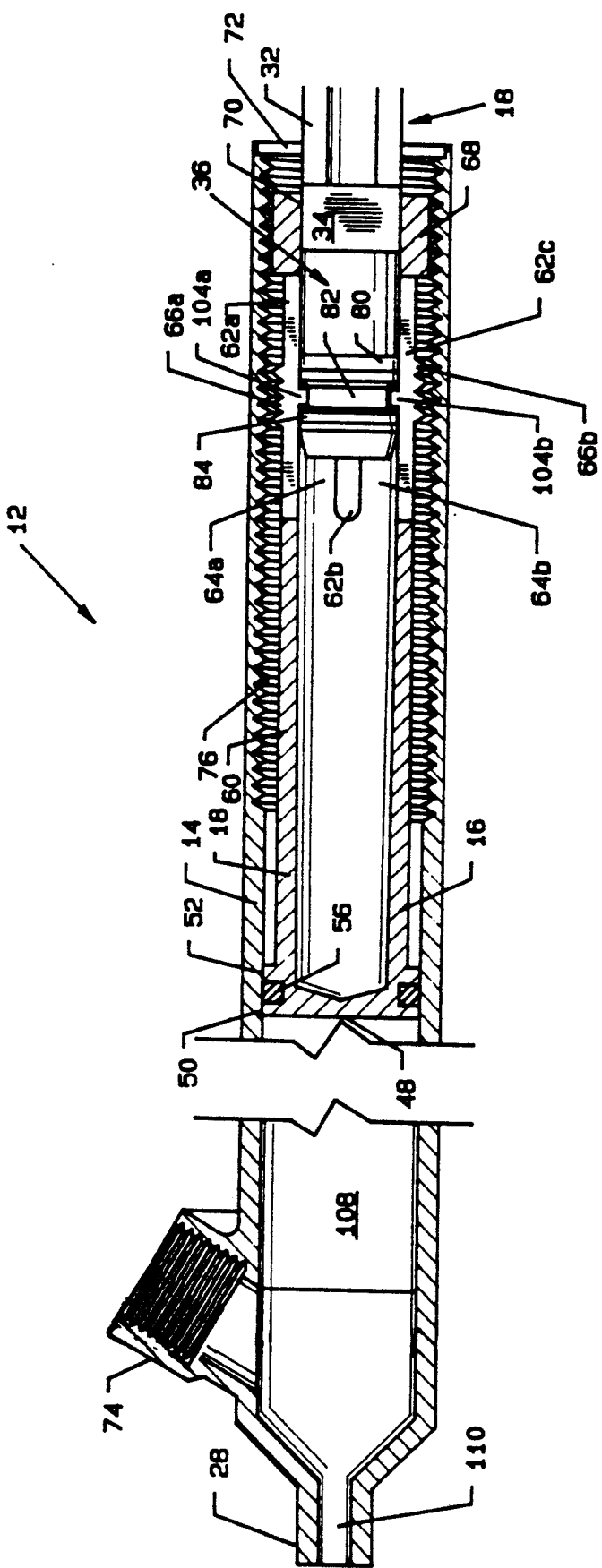
FIG. 10 illustrates the first mode of operation of the inflation system for a balloon catheter.

FIG. 10 illustrates the first mode of operation where the handle 18 and plunger 16 have freedom of movement within the syringe barrel body 14 where the syringe 12 operates in the mode similar to that of a common syringe where contrast media can be drawn into the syringe assembly by outward movement of the plunger 16 and air purged by advancing the plunger 16 inwardly to expel air from the syringe. The cams 104a, 104b (and 104c and 104d) of the spring leafs 64a, 64b (and 64c and 64d) engage the cam 82 of the multi-mode cam 36. The cams 104a-104d in this position are captured between cams 80 and 84 coupling the multi-mode cam 36 and thus the handle 18 to the plunger 16 via the integral leaf springs 64a-64d. In this position, the leaf springs 64a-64d are in the relaxed mode where force is not exerted by the cam 82 upon the cams 104a-104d thus leaving the teeth 66a-66d in the same neutral position as that illustrated in FIG. 6, i.e., the teeth 66a-66d do not engage the threads 76 of the syringe barrel 14. The plunger 16 with the inserted multi-mode cam 36 and the handle 18 are free to move to and fro in the syringe barrel 14. Again, this is the same operation as an everyday syringe.

FIG. 11 illustrates the second mode of operation where the syringe 12 functions as a means to pressurize a distensible or compliment medical device such as a balloon catheter where all numerals correspond to those elements previously described. The handle 18 and plunger 16 are manually moved inwardly and is initially free to move within the syringe barrel 14 as described in FIG. 10. As the plunger 16 advanced inwardly, resistance to movement is encountered by the plunger 16 in the interior 108 of the syringe barrel 14 as the inflation fluid medium is expelled into an external inflation device. When this resistance increases the cams 104a, 104b (and 104c and 104d) on the leaf springs 64a, 64b (and 64c and 64d) are forced up on the cam 80 of the multi-mode cam 36 to cause the threaded surfaces 66a, 66b (and 66c and 66d) to engage threads 76 on the interior of the syringe barrel 14. The plunger 16 automatically locks into position as sufficient pressure is encountered. System pressure can be increased by clockwise rotation of the plunger handle 18. This rotation advances the plunger 16 to increase system pressure to the desired level. This pressure can be read by the gauge 22 of FIG. 1.

The third mode, balloon depressurization can be accomplished slowly or rapidly. Slow deflation and depressurization is accomplished by counter clockwise rotation of the plunger handle 18 to slowly withdraw the plunger 16 from the interior 108 of the syringe barrel 14. This rotation allows direct control of the system pressure decay down to approximately 2 ATM.

Rapid deflation, yet part of the third mode of operation, is accomplished by pulling outwardly on the plunger handle 18 to unlock the plunger 16 from the syringe barrel so that the plunger 16 may be freely retracted. Movement of the handle 18 outwardly disengages the cam 80 of the multi-mode cam 36 from the cams 104a-104d of the plunger 16 and allows the cams 104a-104d on the tensional leaf springs 64a-64d to drop into and engage the cam 82 between the cams 80 and 84. By this action, the threaded surfaces 66a-66d are disengaged from the threads 76 of the syringe barrel 14 thereby causing the plunger 16 to be rotationally uncoupled from the syringe barrel 14 again allowing for free to and fro motion of the plunger 16 within the syringe barrel 14 as described and illustrated in FIG. 10.

FIG. 12 illustrates the fourth mode of operation where suction vacuum is maintained by the syringe 12 where all numerals correspond to those elements previously described. This is accomplished by pulling outwardly on the handle 18 until the plunger 16 locks against the syringe barrel 14. As the plunger 16 is moved outwardly, negative pressure or "vacuum" occurs. When the outward pulling force on the handle 18 exceeds to negative pressure or vacuum felt by the face of the plunger 16 cams 104a-104b (and 104c and 104d) on the leaf springs 64a and 64b (and 64c and 64d) are forced out of the cam 82 of the multi-mode cam 36 and up onto cam 84, thus forcing the leaf springs 64a-64d outwardly to cause a locking engagement of the threaded surfaces 66a-66d with the internal threads 76 of the syringe barrel. This locking engagement holds the plunger 16 in a fixed position relative to the syringe barrel 14. Rotation of the handle 18 counter clockwise allows for increased negative pressure on the inflation system. Locking action occurs at about ½ ATM for locking in a negative pressure. This is accomplished by the make up of the cam 84 and adjacent ramp 96 which have an overall slope gradient less than that of ramps 98 and 100 leading to cam 80 which locks at about 2 ATM during the mode two operation of pressurization.

Figure 13:
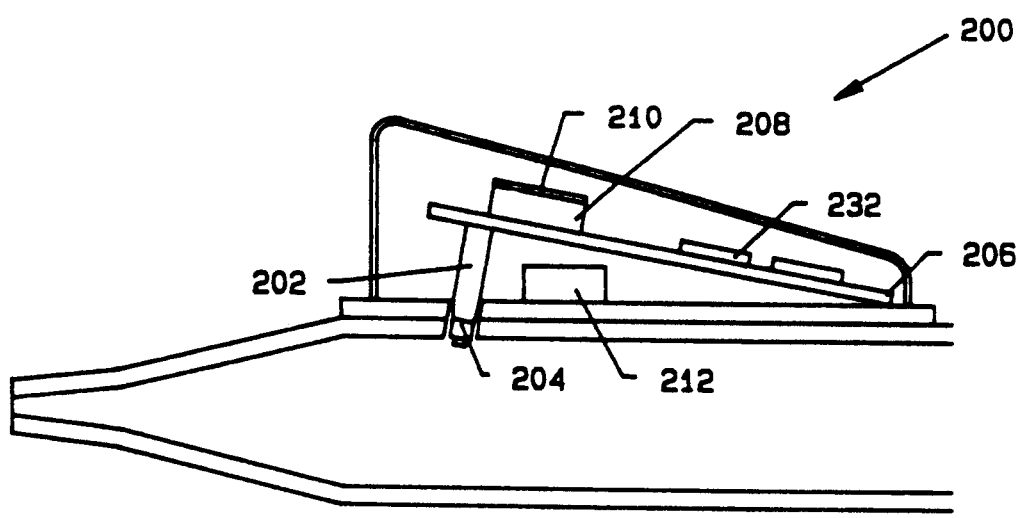
FIG. 13 illustrates a plan view of a digital display for an inflation system for a balloon catheter.

FIG. 13 illustrates a plan view of a digital display system 200 for a balloon catheter inflation system 10. A pressure tube 202 with a strain gauge 204, such as a lithographed strain gauge mounted on the pressure tube 202, engages into a threaded ramped member 74 as a port hole. The digital display system 200 includes a printed circuit board 206 supporting a digital display 208 for displaying pressure in atmospheres and time in seconds for the pressure. The digital display 208 can be a suitable LED or LCD display, such as with a polarizing filter 210. The printed circuit board 206 also supports a microprocessor and other circuitry for processing and storage of pressure, time and date information as later described in detail. A plurality of user interface switches 214 position on a housing 218 supporting elements 206-216. A data communications port 216 connects to the microprocessor through an interface. AN RS232 is an example of a communications protocol, and other protocols can be utilized. The housing connects such as by snap on engagement to the syringe barrel for repeated use in other procedures. A battery 212, such as a 9 volt battery powers the digital display system 200.

Figure 14:
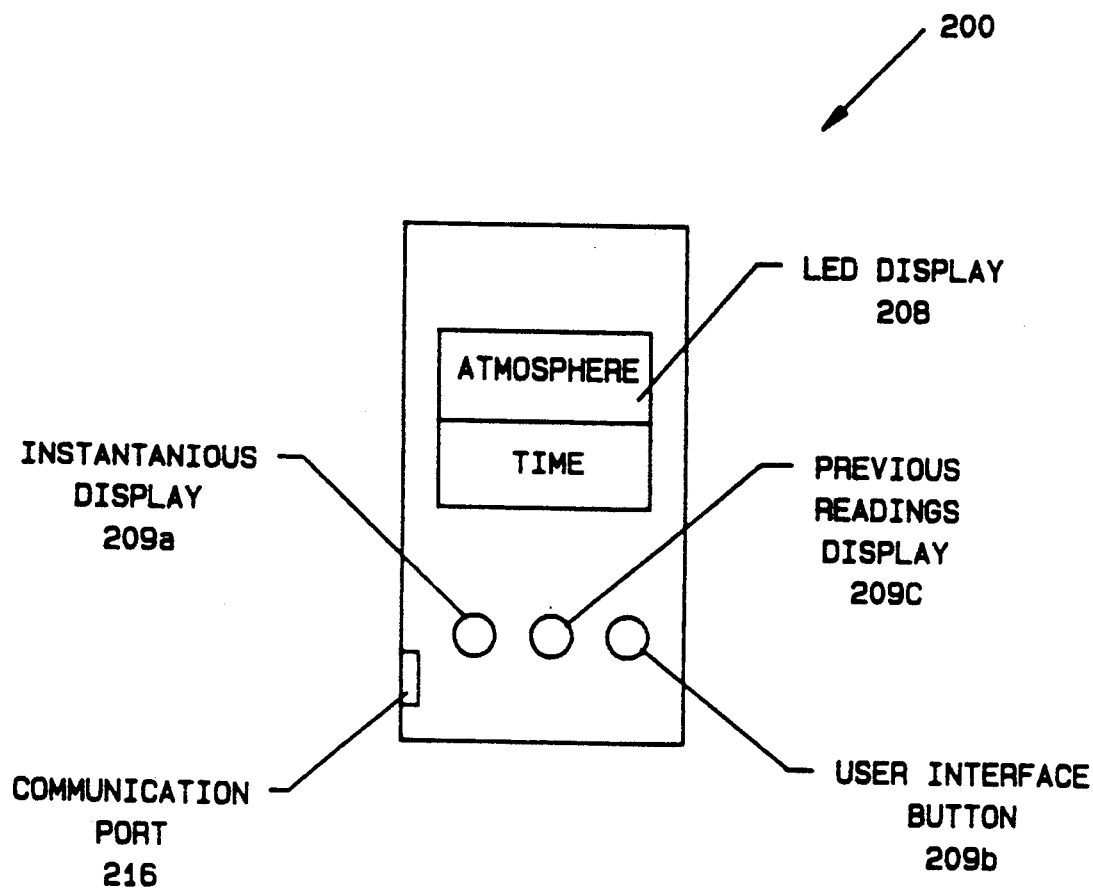
FIG. 14 illustrates a front view of the housing for the digital display system.

FIG. 14 illustrates a front view of the housing for the digital display system 200 including the digital display 208, user interface buttons including an instantaneous display button 209a, a hold display button 209b, and previous readings 209c for call-up of the previous readings.

Figure 15:
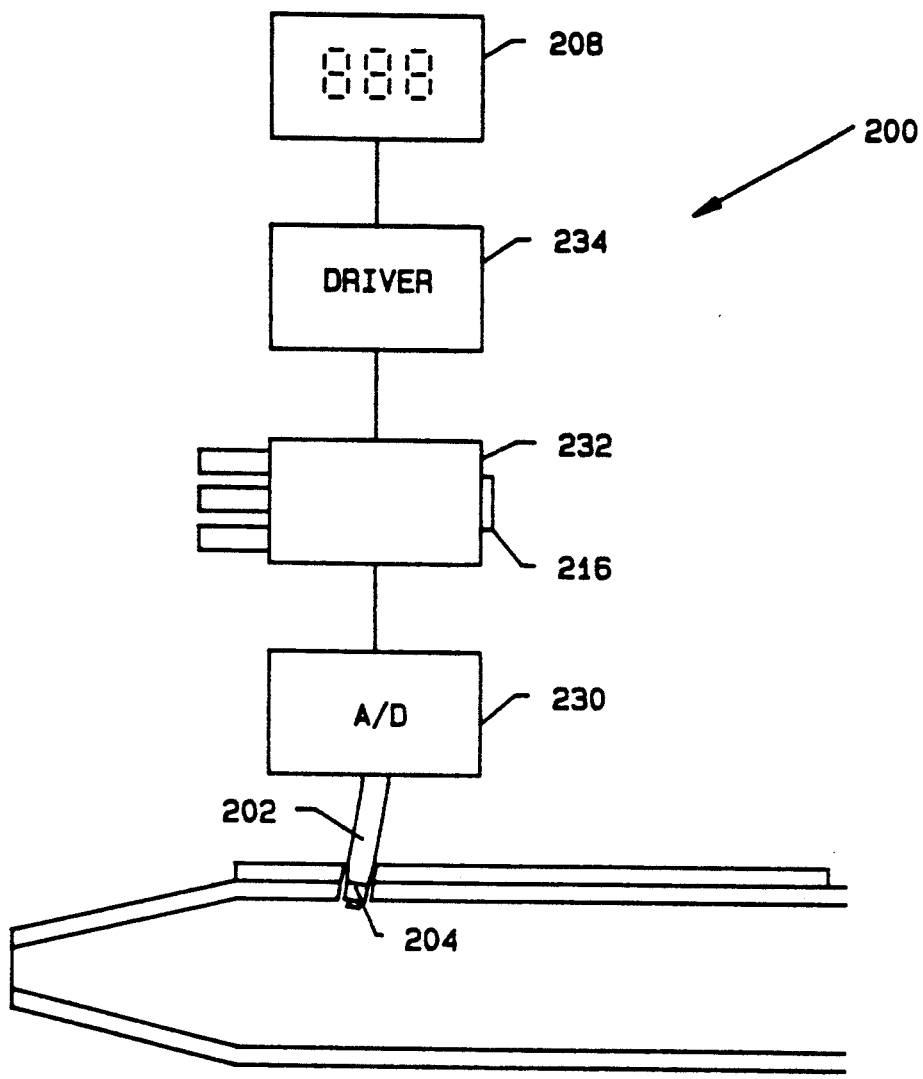
FIG. 15 illustrates an electrical block diagram of a digital display system; and, FIG. 16 illustrates a mode Of operation of the digital display system with a personal computer and optional display systems.

FIG. 15 illustrates a block diagram of the digital display system 200 for the strain gauge 204 generates a signal based on the pressure in the inflation device. An A/D converter 230 connects to the strain gauge 204 to convert the analog signal to a digital signal. The microprocessor 232 connects to the A/D converter 230 to convert the A/D signal to a digital signal for subsequent digital display. The microprocessor 232 also samples and stores pressure readings for finite time periods during angioplasty procedures according to date, time and pressure. Any processing of the digital signal to digital pressure readings are internally processed by the microprocessor 232. A display driver 234 and the digital display 208 connect to the microprocessor 232. The digital display 208 can be an LCD or LED display with appropriate back lighting as may be required. The data communications port 216 connects to the microprocessor 232 through an internal interface on the printed circuit board 206 as may be required.

Figure 16:
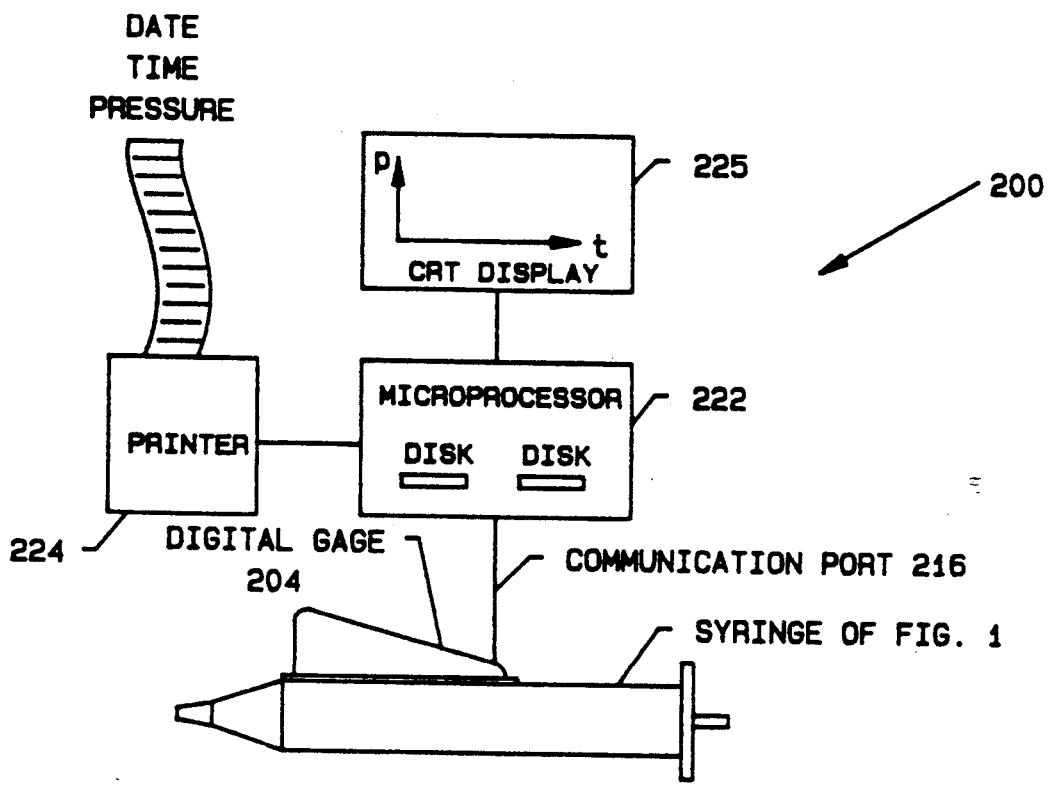

FIG. 16 illustrates an electrical block diagram of the digital display system 200 connected to a personal computer 222. A printer or strip chart recorder 224 and a video display 225 connect to the microprocessor 232. The microprocessor stores date, time and pressure over finite time intervals for later display and hard copy for the medical files.

MODE OF OPERATION

The inflation system accomplishes pressurization by converting mechanical motion into hydraulic energy. In the system, a plunger is designed with screw threads along part of the length. This assembly is contained within a syringe, such that the threads are engaged and axial motion of the plunger can be achieved by turning. As a result, fluid within the inflation device and attached balloon catheter is pressurized. Axial motion of the plunger is continued until the desired pressure is read on the digital display system 200. Generally, inflation devices are capable of pressures up to 20 atmospheres or approximately 300 psi. After pressurization is complete, the plunger motion is reversed, decreasing the pressure until ultimately a vacuum is created to collapse the balloon. The reduced passageway for the pressure sensor isolates the digital display system, as well as providing a medically sterile digital display system.

Various modifications can be made to the present invention without departing from the apparent scope hereof.

We claim:

1. Inflation system for a balloon catheter comprising:
   a. a syringe with an internally threaded barrel and an outlet at the distal end of said barrel;
   b. plunger means adapted for movement in said barrel and including a closed distal end, an open proximal end, at least one outer annular ring about said closed distal end, and threaded expansion means for engaging said internal threads of said barrel when the pressure in said barrel reaches a predetermined pressure level;

c. handle means for insertion through said proximal end of said plunger means and including ramped camming means for camming said threaded expansion means into threaded engagement with said internal thread of said barrel;

d. said threaded expansion means comprises leaf springs defined by a plurality of elongated holes spaced about the circumference of said plunger means, said leaf springs capable of being flexed outwardly by said ramped camming means of said handle means; and, e. pressure sensing means integrally engaged on said barrel for generating a pressure signal in response to a pressure in said inflation system.

* * * * *